(12) United States Patent
Kuo

(10) Patent No.: US 7,442,040 B2
(45) Date of Patent: Oct. 28, 2008

(54) TEMPLATE FOR VENEER APPLICATION

(75) Inventor: Eric E. Kuo, Foster City, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 11/034,625

(22) Filed: Jan. 13, 2005

(65) Prior Publication Data

US 2006/0154207 A1 Jul. 13, 2006

(51) Int. Cl.
A61C 13/08 (2006.01)
(52) U.S. Cl. .................... 433/202.1; 433/173
(58) Field of Classification Search ............... 433/202.1
See application file for complete search history.

(56) References Cited

U.S. PATENT DOCUMENTS

| | | | |
|---|---|---|---|
| 4,473,353 A | 9/1984 | Greggs | |
| 5,501,600 A | 3/1996 | Johnson | |
| 5,527,182 A * | 6/1996 | Willoughby | 433/172 |
| 5,975,893 A | 11/1999 | Chishti et al. | |
| 6,210,162 B1 | 4/2001 | Chishti et al. | |
| 6,217,325 B1 | 4/2001 | Chishti et al. | |
| 6,227,850 B1 | 5/2001 | Chishti et al. | |
| 6,227,851 B1 | 5/2001 | Chishti et al. | |
| 6,299,440 B1 | 10/2001 | Phan et al. | |
| 6,309,215 B1 | 10/2001 | Phan et al. | |
| 6,318,994 B1 | 11/2001 | Chishti et al. | |
| 6,371,761 B1 | 4/2002 | Cheang et al. | |
| 6,386,864 B1 | 5/2002 | Kuo | |
| 6,386,878 B1 | 5/2002 | Pavlovskaia et al. | |
| 6,390,812 B1 | 5/2002 | Chishti et al. | |
| 6,394,801 B2 | 5/2002 | Chishti et al. | |
| 6,398,548 B1 | 6/2002 | Muhammad et al. | |
| 6,406,292 B1 | 6/2002 | Chishti et al. | |
| 6,409,504 B1 | 6/2002 | Jones et al. | |
| 6,450,807 B1 | 9/2002 | Chishti et al. | |
| 6,454,565 B2 | 9/2002 | Phan et al. | |
| 6,457,972 B1 | 10/2002 | Chishti et al. | |
| 6,463,344 B1 | 10/2002 | Pavloskaia et al. | |
| 6,471,511 B1 | 10/2002 | Chishti et al. | |
| 6,485,298 B2 | 11/2002 | Chishti et al. | |
| 6,488,499 B1 | 12/2002 | Miller | |
| 6,497,574 B1 | 12/2002 | Miller | |
| 6,499,997 B2 | 12/2002 | Chishti et al. | |
| 6,705,863 B2 | 3/2004 | Phan et al. | |
| 2003/0194677 A1 | 10/2003 | Sachdeva et al. | |

OTHER PUBLICATIONS

Nazarian, Ara, DDS, "*The Diagnostic Wax-Up: A Blueprint for Success*," Dentaltown Magazine, vol. 5, Issue 12, Dec. 2004, 4 pages.

* cited by examiner

*Primary Examiner*—Cris Rodriguez
*Assistant Examiner*—Candice C Stokes

(57) ABSTRACT

In one aspect, a method for producing digital models of dental positioning appliances includes providing a digital model of a patient's dentition including teeth; providing a digital model of a veneer covering the patient's teeth; positioning the digital model of the veneer on the digital model of the patient's dentition to produce a combined digital model; and fabricating the dental positioning appliance based on the combined digital model. In another aspect, a dental template includes one or more veneer portions adapted to be secured to teeth; and a removable appliance having one or more veneer portion receiving spaces therein, said removable appliance and the veneer portions adapted to be placed on the teeth.

24 Claims, 3 Drawing Sheets

TEMPLATE FOR VENEER APPLICATION

BACKGROUND

The present invention is related generally to the field of orthodontics.

One goal for orthodontic treatments is to improve a patient's cosmetic appearance and dental function. As discussed in U.S. Pat. No. 5,501,600, improving the appearance of one or more of a person's teeth has been undertaken previously by adding an aesthetically appearing porcelain veneer to a respective tooth or teeth.

The veneering process is historically complex, time consuming and expensive. By way of example, U.S. Pat. No. 4,473,353 describes one method for cosmetic restoration of anterior teeth. As discussed therein, a dental professional custom made a glazed porcelain labial veneer for a patient's tooth. Thereafter, he/she chemically and mechanically bonded the glazed porcelain labial veneer to the respective patient's tooth, to provide a healthful and long lasting cosmetic restoration of desired color, shape, and aesthetic appearance. In this method, conventional crown and bridge impression materials were used in taking an impression of the patient's teeth, and recordings were made pertaining to the patient's bite, shade and other pertinent data. The patient's impression was filled by pouring in die stone materials. A "Pindex" model was made, pinning all teeth to be veneered, as well as adjacent teeth. Each tooth die was undercut at the cervical extension, trimmed at the marginal areas of the regions to be veneered and hardened, so as to replicate the identical structure of the cosmetically defective tooth. A triangular shaped platinum foil was placed over the labial surface of the tooth die with the apex pointed downward and forming a tab portion which extends below the gingival margin. The base of the triangular shaped foil was folded over the incisal edge of the die and at least partially around the proximal surfaces, in such a manner as to form a snugly fitting, but hingedly removable at the top, foil sheath on the tooth die. For added retention, the foil was adhered to the previously made undercut. The platinum matrix was removed from the die using the tab portion formed by the foil apex and pulling the foil sheath hingedly off the incisal edge of the die, and the platinum matrix was then held over a Bunsen burner flame to decontaminate it. The platinum matrix was then reapplied to the die and burnished thereon. Porcelain was then applied to the labial surface of the platinum matrix using a brush, starting at the cervical undercut and working up to the incisal edge, and in so doing, the building up of the porcelain was undertaken thinly and uniformly. The platinum matrix (also called the foil matrix) with the porcelain was removed from the tooth die and placed on a tray, then in turn placed in a furnace for firing. The foil matrix and baked porcelain veneer thereon were then replaced on the tooth die. The marginal areas of the porcelain veneer were finished. Then the porcelain veneer was contoured into an aesthetic shape, and the labial anatomy was carved. The foil matrix and the porcelain veneer were removed from the tooth die for the last time, and the porcelain veneer was cleaned ultrasonically. Then the porcelain veneer was stained and glazed using conventional techniques to conform to the shade characteristics selected in respect to the patient's teeth. The room temperature foil matrix and porcelain veneer were placed in distilled water for one minute. Then using tweezers, the foil was gently removed from the porcelain veneer, leaving a thin clearance for the cement used to bond the veneer to the tooth. The intaglio, or inside surface, of the porcelain veneer was then etched, usually by air abrasion, to promote bonding thereof to the enamel tooth surface. Then the appropriate enamel surfaces of the patient's tooth were etched with an acid gel formulation, to create micropores in the tooth and thereby promote bonding. The intaglio surface of the porcelain veneer was then coated with a thin layer of light cured bonding agent, and a similar layer of the bonding agent was applied to the etched enamel bonding surface of the patient's tooth. Both of these layers of bonding agent were polymerized by light curing; and a coating of dental filler material was then applied to either the patient's tooth or the intaglio surface of the porcelain veneer. The porcelain veneer was placed onto the patient's tooth; excess filler material was trimmed away, and the filler material was polymerized by a second application of light; and the dentist finished the proximal and incisal margins to provide a smooth restoration surface.

U.S. Pat. No. 5,501,600 provides a method wherein a noble metal foil matrix, which conforms to the front tooth die of a patient, and a porcelain ceramic slurry, which will be applied to the metal matrix, are quickly and accurately obtained. The improved method of providing the porcelain ceramic slurry involves leaving a central area of the noble metal foil matrix uncovered during a first firing period to obtain the first layer of porcelain veneer. Leaving this initial area uncovered compensates for the shrinkage of the porcelain during the first firing period.

On a parallel note, removable dental positioning appliances with attachments are available. As discussed in U.S. Pat. No. 6,705,863, such removable dental positioning appliances usually comprise an elastic polymeric shell having a cavity for receiving at least some of a patient's teeth and are often preferred over conventional braces for tooth repositioning due to comfort, appearance and ease of use. These appliances function by applying force to specific surfaces of the teeth or dental features to cause directed movement. However, the type of movement and level of force applied is usually dependent on the surface characteristics and positions of the dental features. In many cases, the native tooth surface (s) and other dental features of a patient are inadequate to provide sufficient anchoring or to impart sufficient force on the teeth to be repositioned. To overcome these limitations, one or more attachment devices may be attached to preselected attachment points on the teeth or dental features to provide the appropriate physical leverage. Specific design and location of these attachment devices may provide newly achievable and/or more effective repositioning forces, anchoring ability and appliance retention. The use of attachment devices in combination with removable dental positioning appliances provides the patient with the benefits of removable appliances while retaining the ability to extrude, rotate, and otherwise manipulate teeth as with conventional braces. Like conventional braces, attachment devices may be bonded to the surface of the teeth in order to provide physical features which facilitate the application of controlled force. The attachment devices may have a very simple construction, in some instances being only a bump, bead, wedge, or other body or structure which can be fixedly attached to the surface of a tooth or other dental feature in order to transmit force generated by the dental positioning appliance to the dental feature and/or to anchor the positioning appliance to teeth in order to permit the appliance to apply forces elsewhere in the patient's teeth. These attachments may either be preformed and positioned into place using an aligner template as the positioning device, or they may be simultaneously created and bonded using a polymerizable material which is attached into the desired precise position using an attachment template. In either case it is the attachment template which facilitates bonding of the attachment at the desired position on the tooth.

SUMMARY

In one aspect, a method for producing digital models of dental positioning appliances includes providing a digital model of a patient's dentition including teeth; providing a digital model of a veneer covering the patient's teeth; positioning the digital model of the veneer on the digital model of the patient's dentition to produce a combined digital model; and fabricating the dental positioning appliance based on the combined digital model.

Implementations of the above aspect may include one or more of the following. The method can provide a digital model of the patient's dentition by scanning the patient's prepared teeth. For ceramic or indirect composite veneers, the digital model of the patient's dentition can come from scanning a mold of the patient's prepared teeth, or by scanning the patient directly using a 3-D imaging scanner such as a cone-beam CT machine (CBCT). A "virtual" computerized veneer model can be generated from the patient's digital model of the prepared dentition. The 3-D model of the virtual veneer can then be converted into a wax model via 3-D printing. A negative mold can be created from the physical 3-D wax model. Porcelain can be casted into the negative mold to form the veneer. The 3-D virtual model of the veneered dentition can be built into a 3-D solid model using a stereolithography apparatus (SLA). From this 3-D model, a thermoformed template can be created, and this template used to accurately position the veneers into the same position as indicated in the virtual model.

The thermoformed dental template/appliance can be made from a thin shell material. The polymeric appliance is preferably formed from a thin sheet of a suitable elastomeric polymeric. The veneer can be positioned on the template and upon confirmation of esthetics, a professional can attach the veneer to the teeth. The template prevents veneer from floating. The veneer can be secured to one or more teeth with cement or epoxy. The template can be removed afterward, leaving the veneer on the teeth. One or more veneer portions can be positioned on one template for mounting at the same time. Alternatively, one or more veneer portions can be mounted on a plurality of templates over one or more installations.

For direct composite veneers where the veneer is made of a polymerizable composite material that is hardened directly on the teeth, the teeth may be scanned as partially prepared teeth, fully prepared teeth model (as with ceramic veneers) or as unprepared model or as a wax set-up. A veneered dentition model can be generated from the patient's digital model to create a 3-D virtual model of the desired final outcome. The 3-D virtual model of the veneered dentition can be built into a 3-D solid model using a stereolithography apparatus (SLA). From this 3-D SLA model, a thermoform template can be created, and this template filled with unpolymerized dental composite. The teeth are prepared to receive the uncured dental composite with etchant and adhesive resin, and the template is placed on top of the teeth. The composite and adhesive are then cured into the desired place, as the template ensures that the contours of the veneer are equivalent to the contours created in the virtual 3-D model.

In another aspect, a dental template includes one or more veneer portions adapted to be secured to teeth; and a removable appliance having one or more veneer portion receiving spaces therein, said removable appliance and the veneer portions adapted to be placed on the teeth. The veneer-positioning dental template can be used even where the veneers themselves are not created virtually and made from a 3-D printout. In this embodiment, steps 14-20 are skipped in lieu of traditional veneer fabrication steps. A veneer set on a stone die can be scanned electronically to generate a 3-D model, from which a 3-D model is created and a template formed from the 3-D model. This template can then be used to help position the veneer in the correct position.

One aspect of the system supports the creation of "direct" composite veneers such as Cerinate. In contrast to making direct composite veneers by free-hand today (the doctor shapes the veneers without a physical guide) the instant veneer template is computer fabricated and would make the outcomes more consistent and efficient. The template is created either from a virtual veneer on a scanned tooth, or by scanning a waxed-up mock version of the desired final outcome. A 3-D template is made from this model using the SLA/aligner formation to provide a "negative" of the desired final outcome. Instead of placing a preformed veneer into the template, in direct composites, the doctor would fill the uncured composite resin inside the template and snap the template on the teeth. The resin is cured into place on the prepared or unprepared teeth directly. The template is removed and the resin remains on the teeth in the desired shape and size.

In another aspect, an electronic model of the veneered final outcome can be created by either scanning the veneer sitting on the die, or by scanning a wax or composite mock up by way of all the different scan techniques mentioned. The template is created using SLA from the scanned veneer/die or mockup. The positioning of the veneers is more accurate, and the 3-D virtual veneer fabrication element can be separated from the process.

The veneer template allows veneer to be accurately positioned on teeth regardless of tooth surface variations from the norm that the veneer is designed for. The treatment can be done virtually and the placement of the veneers can be done using a template device that is a removable guide. The template allows precise placement of the veneers and enables veneer placement onto specific teeth independent of overall arch geometry. The template makes it easier for a less well-trained or an untrained person to bond the veneers. The system minimizes variations in the perception of distance and angles. The template provides a very precise control on the placement of the veneers. The resulting treatment can change the color, size or shape of existing teeth and create a whole new smile.

DESCRIPTION

Figure 1:
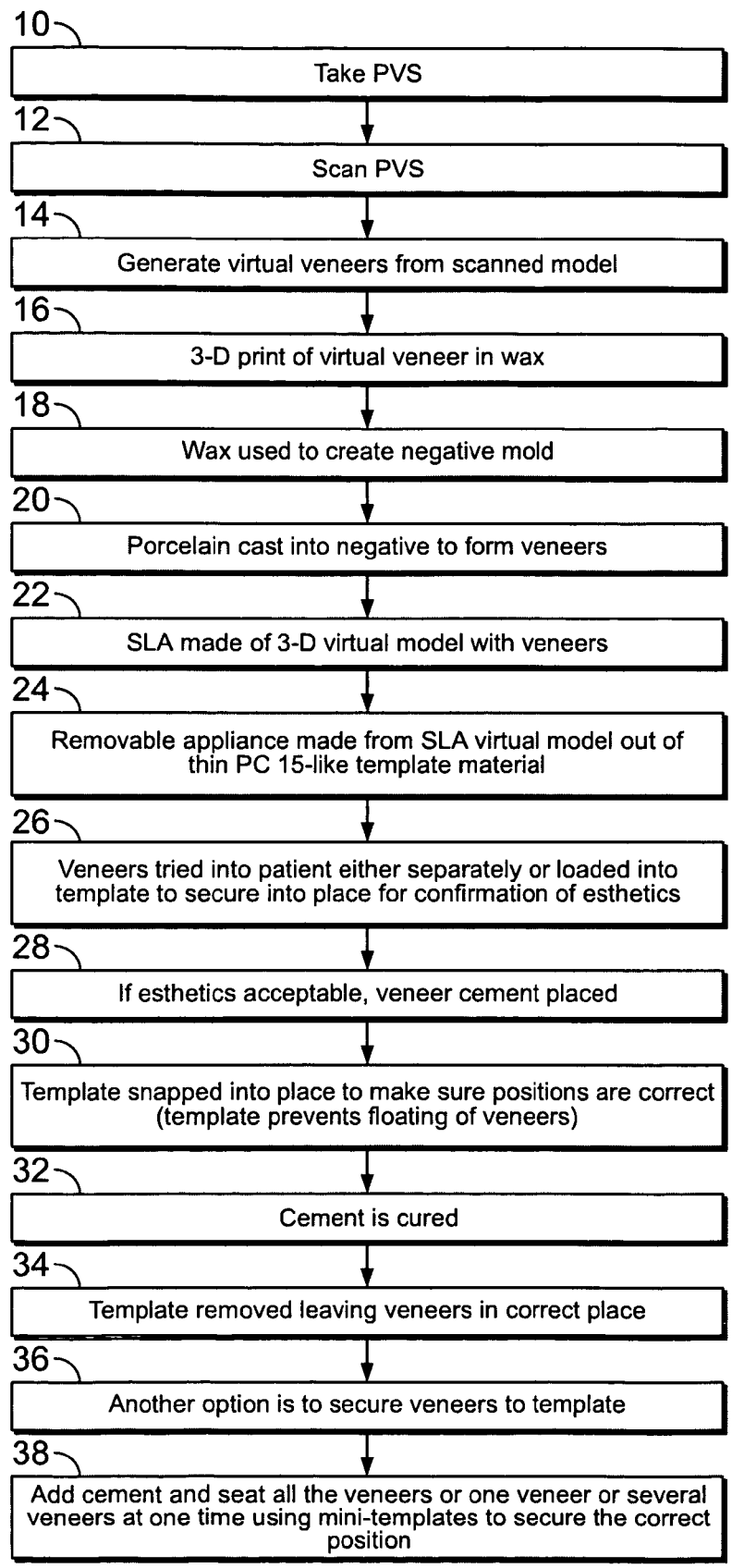
FIG. 1 shows an exemplary process to create a template to install veneer over teeth.

FIG. 1 shows an exemplary process to create a template to install veneer over teeth. First, a PVS impression is taken of either the prepared or unprepared teeth (10). Next, the PVS impression is scanned or digitized into a 3D digital model (12). This model may also be obtained in a variety of other ways. For example, the patient's teeth may be scanned or imaged using well known technology, such as X-rays, threedimensional x-rays, computer-aided tomographic images or data sets (including cone-beam computer-aided tomography), magnetic resonance images, among others. Methods for digitizing such conventional images to produce data sets useful in the present invention are well known and described in the patent and medical literature. The data set produced by the range acquisition system may, of course, be converted to other formats to be compatible with the software which is used for manipulating images within the data set as known in the art.

Based on the digital model, the process generates virtual veneers (14). A 3-D physical wax model is created from the virtual veneer (16). The wax is used to create negative mold (18). Porcelain or dental composite is then cast into a negative to form veneers (20). Other dental materials besides porcelain and dental composite may be used to form the materials depending on the material properties desired in the veneer.

A rapid prototyping machine such as a stereolithography apparatus (SLA) is used to make a 3-D virtual model of the dentition with veneers in place (22). A removable appliance is made from SLA virtual model (24). The dental template/appliance can be formed and can be made from a thin shell material. The polymeric appliance is preferably formed from a thin sheet of a suitable elastomeric polymeric, such as Tru-Tain 0.030 in. thermal forming dental material, Tru-Tain Plastics, Rochester, Minn. 55902. Usually, no wires or other means will be provided for holding the appliance in place over the teeth. In one implementation, the appliance is made from a thin material such as PC15 (polycarbonate 0.015 inch) available from Align Technology, Inc.

Veneers are then mounted on the patient's teeth either separately or as a group by loading the veneers into the template that secures the veneers into place for confirmation of esthetics (26). In one embodiment, porcelain veneers are used. Because they are glass-like, the veneers have a great advantage over other types of cosmetic dental bonding by the fact that they are translucent. When they are bonded onto a tooth's surface they mimic the light handling characteristics of enamel. Light striking a porcelain veneer will penetrate its thickness, and then subsequently be reflected back out once it has reached the opaque cement and tooth structure lying underneath the veneer. This translucency effect provides a sense of depth, and thus a very life-like appearance. Another advantage of porcelain veneers over other types of cosmetic dental bonding is related to the fact that a porcelain veneer's surface is just that, porcelain. Since porcelain is a ceramic, and therefore glass-like, its surface is smooth and impervious. Thus, the surface of a porcelain veneer will resist staining from smoking, for example.

In a second embodiment, cured dental composite resin is used. Dental composite veneers that have been cured to form a veneer "indirectly" (not directly on the tooth structure) enables the material to complete any polymerization shrinkage without straining the tooth, and can be processed so that the resin material is much more fully cured than if the material is cured directly on the teeth.

In general, when preparing a tooth for a porcelain or composite veneer, the enamel on the front side of the tooth, the side where the porcelain veneer will be bonded, may need to be trimmed back. Usually the teeth are trimmed to about the same amount as the thickness of the veneer that will ultimately be bonded into place. This way, the net size of the teeth will not be dramatically changed.

Before a dentist can bond the porcelain veneer into place, the doctor will need to evaluate its fit on the tooth. To do so, the doctor positions the veneer on the prepared tooth with a holding paste or gel, inspects it, removes the veneer, and trims it repeatedly, until both the doctor and patient are satisfied. Moreover, the doctor determines the appropriateness of the veneer's color. Because porcelain and composite veneers are thin and thus translucent, the precise color a veneer will possess can be adjusted by changing the shade of the cement, which is used to bond the veneer into place.

Once the patient and the doctor agree that the shape and shade of the veneer is appropriate, it can be bonded into place. If the esthetics are acceptable, veneer cement is applied to the teeth (28) and the veneers positioned atop the cement. The positioning template is then snapped into place to ensure that the veneer positions are correct (the template prevents the floating of veneers) (30). The cement is cured (32). Next, the template is removed leaving veneers in correct place (34).

Another option is to first secure the veneers to the positioning template (36) using adhesive cement or suitable epoxy. The epoxy can be used to pick up or transfer the veneers from the stone die into the template for delivery onto the patient in the same position as on the die. Further, the process can secure all the veneers at once using one template. Alternatively, several veneers can be installed using a plurality of templates to secure the veneer to the correct position (38). The template may require surface preparation or perforation in order to secure the veneer to the template with the epoxy adhesive.

Additionally, the veneer may be made from a variety of materials, including materials which have been formulated to be sensitive to an environmental condition or external stimulus. For example, upon exposure, a malleable material may become rigid, allowing changes in geometry to be made in the malleable state. This may be particularly useful in conforming the geometry of a veneer to better interface an uneven or curved surface. The material may be exposed to a stimulus to which it is sensitive, initiating a state change in the material. Such a stimulus may be a change in the oral environment to a non-physiologic pH, temperature, ionic strength or liquid absorption. Likewise, the stimulus may be of an external source such as light, heat, magnetism, electricity, radiowaves, or chemicals. Likewise, polymerization may occur over time from the point of initial formulation, as in the case of an air or moisture cure. Polymerization may simultaneously harden the material and form a bond between the material and any interfacing surface.

A series of methods are provided based on these polymerization characteristics to produce and/or bond the veneer to a tooth. Three preferred embodiments are applicable for use with elastic positioning appliances and are as follows: 1) basic casting, 2) casting with polymerizing material and 3) computer-aided casting with polymerizing material.

Figure 2:
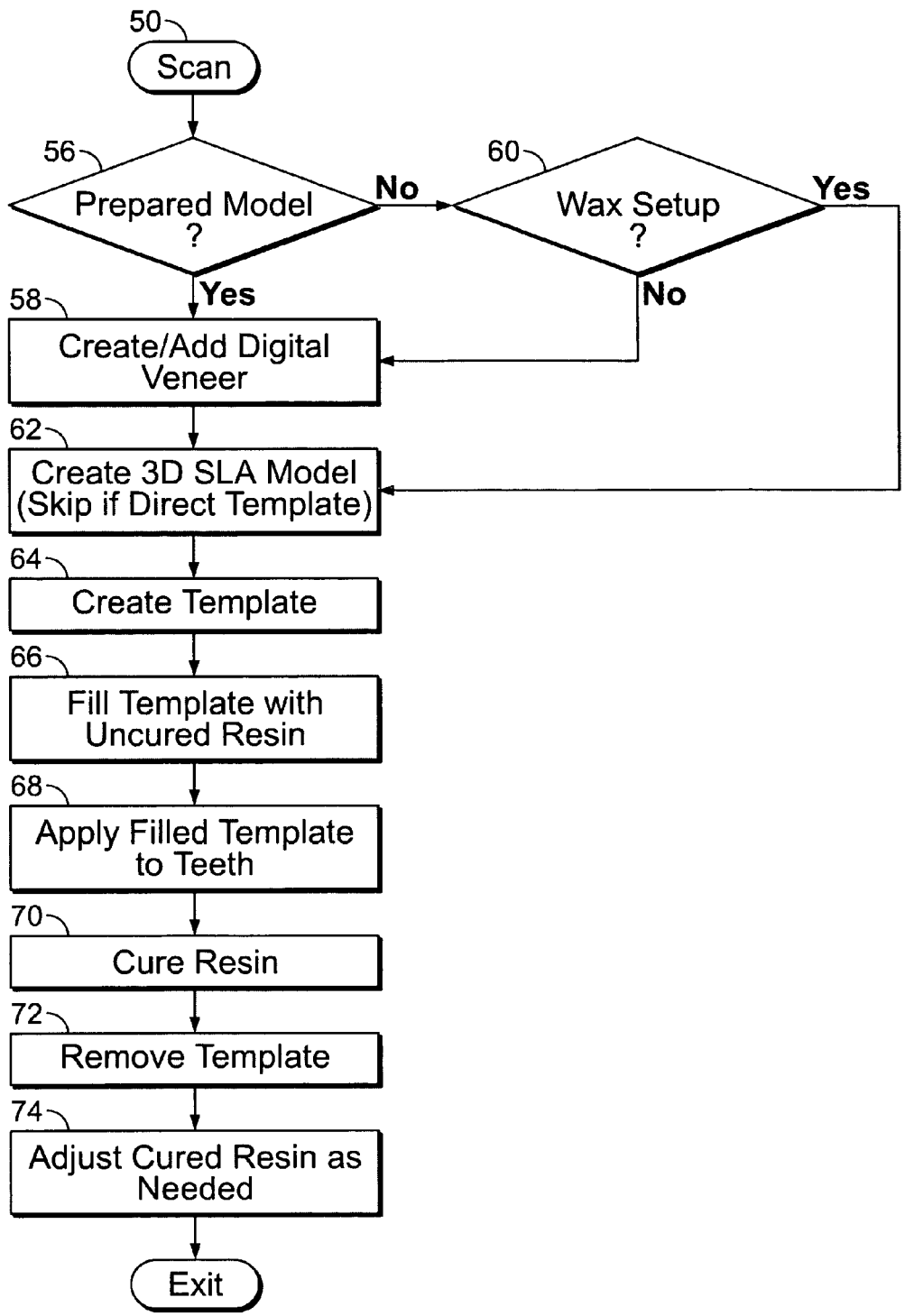
FIG. 2 shows another exemplary process to create a template to install veneer over teeth.

FIG. 2 shows another exemplary process to create a template to install veneer over teeth. In this process, the patient's teeth are scanned (50). Next, for prepared teeth model approach (56), or if wax-setup is not done (60), a digital veneer model is created or added (58) before proceeding to step 62. Alternatively, for wax set-up approach (60), the 3D stereolithography apparatus (SLA) model is created (62). Step 62 can be skipped if the template is to be directly fabricated using SLA. The template is formed (64), and the template is filled with uncured resin (66). The template with the resin is applied to the patient's teeth (68) and the resin is cured (70). The template is removed (72), and the cured resin can be adjusted as needed (74).

Figure 3:
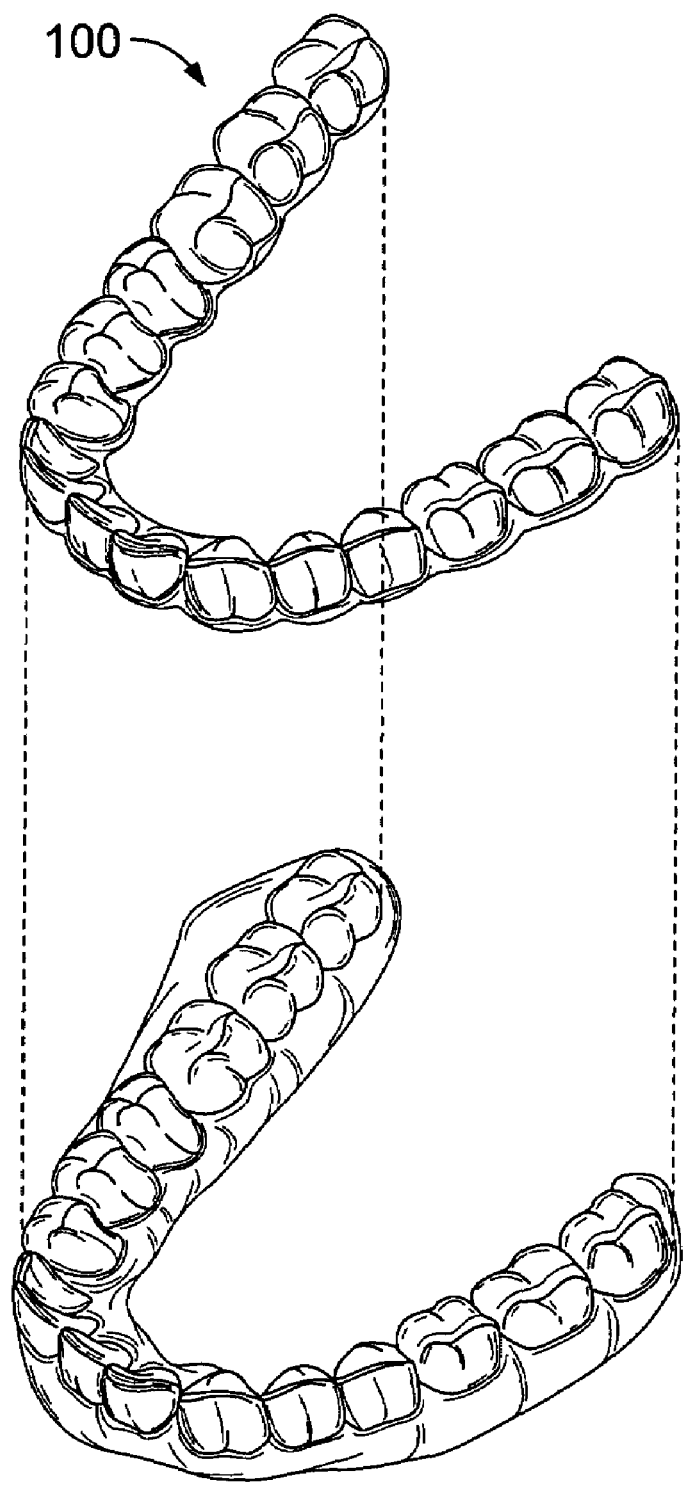
FIG. 3 shows an exemplary veneer template positioned above the patient's teeth for installation.

FIG. 3 shows one exemplary template 100 with veneer portions positioned on the bottom of the template 100. The template 100 with veneers can be positioned over a model for aesthetic review and approval from the patient prior to teeth bonding operations. Once approval is granted, the template 100 is then inserted over the teeth during veneer installation.

After installation, the template 100 can be peeled off or otherwise disposed of, leaving only the veneer on the teeth.

More information on the fabrication of the dental template or appliance is disclosed in U.S. Pat. No. 6,499,997 "Manipulable dental model system for fabrication of a dental appliance"; U.S. Pat. No. 6,497,574 "Modified tooth positioning appliances and methods and systems for their manufacture"; U.S. Pat. No. 6,488,499 "Methods for correcting deviations in preplanned tooth rearrangements"; U.S. Pat. No. 6,485,298 "System and method for releasing tooth positioning appliances"; U.S. Pat. No. 6,471,511 "Defining tooth-moving appliances computationally"; U.S. Pat. No. 6,463,344 "Efficient data representation of teeth model"; U.S. Pat. No. 6,457,972 "System for determining final position of teeth"; U.S. Pat. No. 6,454,565 "Systems and methods for varying elastic modulus appliances"; U.S. Pat. No. 6,450,807 "System and method for positioning teeth"; U.S. Pat. No. 6,409,504 "Manipulating a digital dentition model to form models of individual dentition components"; U.S. Pat. No. 6,406,292 "System for determining final position of teeth"; U.S. Pat. No. 6,398,548 "Method and system for incrementally moving teeth"; U.S. Pat. No. 6,394,801 "Manipulable dental model system for fabrication of dental appliances"; U.S. Pat. No. 6,390,812 "System and method for releasing tooth positioning appliances"; U.S. Pat. No. 6,386,878 "Systems and methods for removing gingiva from teeth"; U.S. Pat. No. 6,386,864 "Stress indicators for tooth positioning appliances"; U.S. Pat. No. 6,371,761 "Flexible plane for separating teeth models"; U.S. Pat. No. 6,318,994 "Tooth path treatment plan"; U.S. Pat. No. 6,309,215 "Attachment devices and method for a dental appliance"; U.S. Pat. No. 6,299,440 "System and method for producing tooth movement"; U.S. Pat. No. 6,227,851 "Manipulable dental model system for fabrication of a dental appliance"; U.S. Pat. No. 6,227,850 "Teeth viewing system"; U.S. Pat. No. 6,217,325 "Method and system for incrementally moving teeth"; U.S. Pat. No. 6,210,162 "Creating a positive mold of a patient's dentition for use in forming an orthodontic appliance"; and U.S. Pat. No. 5,975,893 "Method and system for incrementally moving teeth," the contents of which are hereby incorporated by reference.

Various alternatives, modifications, and equivalents may be used in lieu of the above components. Moreover, the veneer template can also position the veneer in any arbitrary 3D position to support a predetermined angulation and inclination specification for the veneers. In that case, the template would fix the veneers in space relative to the tooth. Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner. Further, while the invention has been shown and described with reference to an embodiment thereof, those skilled in the art will understand that the above and other changes in form and detail may be made without departing from the spirit and scope of the following claims.

What is claimed is:

1. A method for producing digital models of dental positioning appliances, said method comprising:
   providing a digital model of a patient's dentition including teeth;
   providing a digital model of a veneer covering the patient's teeth;
   positioning the digital model of the veneer on the digital model of the patient's dentition to produce a combined digital model; and
   fabricating the dental positioning appliance based on the combined digital model.

2. The method of claim 1, wherein providing a digital model of the patient's dentition comprises scanning the patient's teeth.

3. The method of claim 1, wherein providing a digital model of the patient's dentition comprises scanning a mold of the patient's teeth.

4. The method of claim 1, comprising generating a veneer model form the patient's digital model.

5. The method of claim 1, comprising printing a 3-D model of virtual veneer.

6. The method of claim 5, wherein the 3D model is a wax model.

7. The method of claim 5, comprising creating a negative mold from the 3D model.

8. The method of claim 7, comprising casting porcelain, glass, or dental composite into the negative mold to form the veneer.

9. The method of claim 1, comprising forming a 3-D virtual model with the veneer.

10. The method of claim 9, wherein the 3D virtual model is made using stereolithography apparatus (SLA).

11. The method of claim 10, comprising forming the dental appliance.

12. The method of claim 11, wherein the dental appliance is made from a thin template material.

13. The method of claim 1, comprising mounting the veneer on patient directly.

14. The method of claim 1, comprising mounting the veneer on a template.

15. The method of claim 14, wherein upon confirmation of esthetics, attaching the veneer to the teeth.

16. The method of claim 12, wherein the template prevents veneer floating.

17. The method of claim 1, comprising cementing the veneer to one or more teeth.

18. The method of claim 1, comprising removing the template and leaving the veneer on the teeth.

19. The method of claim 1, comprising mounting one or more veneer portions on one template.

20. The method of claim 1, comprising mounting one or more veneer portions on a plurality of templates.

21. A dental template, comprising:
   one or more veneer portions adapted to be secured to teeth, wherein the one or more veneer portions comprise direct composite veneers, and the one or more veneer portions are created from one of: a virtual veneer on a scanned tooth, and a scanned waxed mock version of a desired final outcome;

a removable appliance having one or more veneer portion receiving spaces therein, said removable appliance and the veneer portions adapted to be placed on the teeth;

an uncured resin placed inside the dental template, wherein the dental template is positioned on the teeth.

22. The template of claim 21, wherein the template comprises a "negative" of a desired final outcome.

23. The template of claim 21, wherein the template is removed and the resin remains on the teeth in the desired shape and size.

24. A dental template, comprising:

one or more veneer portions adapted to be secured to teeth;

a removable appliance, formed directly or indirectly, having one or more veneer portion receiving spaces therein, said removable appliance and the veneer portions adapted to be placed on the teeth, and wherein an indirectly formed appliance is made from an SLA mold.

* * * * *